(12) United States Patent
Sakata et al.

(10) Patent No.: US 6,204,394 B1
(45) Date of Patent: Mar. 20, 2001

(54) METHOD FOR PREPARING OXY-DIPHTHALIC ANHYDRIDES

(75) Inventors: Junichi Sakata; Shinsuke Inoue; Shinichi Kadono, all of Fukuyama (JP)

(73) Assignee: Manac Inc., Hiroshima (JP)

( * ) Notice: Subject to any disclaimer, the term of this patent is extended or adjusted under 35 U.S.C. 154(b) by 0 days.

(21) Appl. No.: 09/341,860

(22) PCT Filed: Dec. 1, 1998

(86) PCT No.: PCT/JP98/05390

§ 371 Date: Jul. 14, 1999

§ 102(e) Date: Jul. 14, 1999

(87) PCT Pub. No.: WO99/28287

PCT Pub. Date: Jun. 10, 1999

(30) Foreign Application Priority Data

Dec. 2, 1997 (JP) .................................................. 9-331456
May 7, 1998 (JP) ................................................. 10-124937

(51) Int. Cl.$^7$ ........................ C07D 307/89; C07D 407/12
(52) U.S. Cl. ........................ 549/241; 549/243; 549/310
(58) Field of Search ................................. 549/310, 241, 549/243

(56) References Cited

U.S. PATENT DOCUMENTS 5,153,335 * 10/1992 Stults .

* cited by examiner

Primary Examiner—Joseph K. McKane
Assistant Examiner—Taofiq A. Solola
(74) Attorney, Agent, or Firm—Rodman and Rodman

(57) ABSTRACT

Disclosed is a method for preparing oxy-diphthalic anhydrides, which comprises reacting a halo-phthalic anhydride represented by the formula (1):

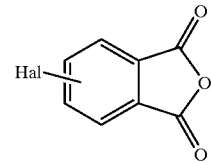

(1)

where Hal represents F, Cl, Br or I, with a carbonate salt selected from the group consisting of lithium carbonate, sodium carbonate, magnesium carbonate and calcium carbonate in a solvent to prepare oxy-diphthalic anhydrides represented by the formula (2):

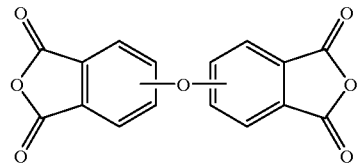

(2)

9 Claims, No Drawings

METHOD FOR PREPARING OXY-DIPHTHALIC ANHYDRIDES

This is a 371 of PCT/JP98/05390 filed Dec. 1, 1998.

FIELD OF THE INVENTION

The present invention relates to a method for preparing oxy-diphthalic anhydrides. The oxy-diphthalic anhydride is important as a starting material for preparing polyimide(s) by reacting with various diamine(s).

BACKGROUND ART

Various methods for preparing oxy-diphthalic anhydrides have been described in literatures. In the old time, there was a method based on an oxidation reaction of tetramethylphenyl ether proposed by Marvel et al. (J. Am. Chem. Soc. 80, 1197-(1955)). This oxidation reaction is inappropriate from the view point of the industrial preparation, since potassium permanganate with high toxicity is employed as an oxidant. Further, in Japanese Provisional Patent Publication No. 122738/1978, there has been described a method for obtaining oxy-diphthalic anhydrides by reacting a halogenated (halo-) phthalic anhydride with caustic soda in a polar solvent, but the yield of the product prepared by this reaction is extremely low. Japanese Provisional Patent Publication Nos. 136246/1980 and 127343/1980 describe a method for preparing oxy-diphthalic anhydrides by reacting a nitro-phthalic anhydride with sodium nitrite and a carbonate salt in a polar solvent. These methods are hardly used for industrial purposes since a harmful nitric oxide is by-produced during the reaction.

In Japanese Provisional Patent Publication No. 96183/1988, there has been disclosed a method for preparing oxy-diphthalic anhydrides by reacting a halo-phthalic anhydride with potassium carbonate and potassium fluoride or cesium fluoride in a polar solvent. However, this method is based on the reaction in which water participates, and can not provide a sufficient yield because of the low reaction ratio caused by the existence of water.

Japanese Patent Publication No. 50071/1991 discloses a method for obtaining oxy-diphthalic anhydrides by dehydrohalogenating a hydroxy-phthalic anhydride and a halo-phthalic anhydride in the presence of potassium carbonate. However, this method is required to prepare the hydroxy-phthalic anhydride by hydrolysis of a halo-phthalic anhydride, thus it can not be said to be an industrially advantageous preparation method.

In Japanese Provisional Patent Publication No. 254673/1989, there has been disclosed a method for directly preparing oxy-diphthalic anhydrides directly by reacting a halo-phthalic anhydride with potassium carbonate in the presence of a potassium fluoride catalyst. This method requires to stir carefully because this method is based on the neat reaction or the similar reaction thereto, thus it is difficult to allow the reactivity to stabilize. In addition, in this method, potassium carbonate can be used restrictedly, and when another carbonate salt such as sodium carbonate is employed in place of potassium carbonate in this method, the reactant shows a high viscosity and the reaction cannot be completed because the reactant does not show any sufficient flowability.

SUMMARY OF THE INVENTION

The present invention relates to a method for preparing oxy-diphthalic anhydrides, which comprises reacting a halo-phthalic anhydride represented by the formula (1):

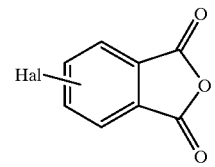

(1)

where Hal represents F, Cl, Br or I, with a carbonate salt selected from the group consisting of lithium carbonate, sodium carbonate, magnesium carbonate and calcium carbonate in a solvent to prepare oxy-diphthalic anhydrides represented by the formula (2):

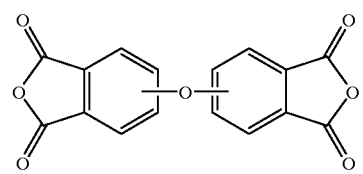

(2)

DESCRIPTION OF THE PREFERRED EMBODIMENTS

According to the present invention, oxy-diphthalic anhydrides can be prepared by employing a carbonate salt other than potassium carbonate and a solvent in the reaction. The shape of the carbonate salt may be powdery or granular, and preferably, the use of the granular carbonate salt leads to more effective reaction. For example, it has been found that the product can be obtained with the reaction ratio of 90% when granular sodium carbonate called typically "soda ash" is employed.

The carbonate salt which can be employed is selected from the group consisting of lithium carbonate, sodium carbonate, magnesium carbonate and calcium carbonate, and preferably sodium carbonate. Where the reaction is carried out in a solvent employing potassium carbonate, it can not provide the predetermined reaction ratio because the reaction cannot be completed. The shape of the carbonate salt, which can be employed in the method of the present invention, may be powdery or granular, and the preference is the granular carbonate salt having the diameter of preferably 50–750 $\mu$m and more preferably 150–750 $\mu$m. From the view point of the yield, the molar ratio of the carbonate salt to the halo-phthalic anhydride is advantageously in the vicinity of about 0.5, and the preferred molar ratio is 0.5–0.4.

The reaction temperature, at which the method of the present invention is carried out, is generally within the range of 170–260° C. The employable catalyst is a phosphonium salt or a sulfonium salt which is a phase transfer catalyst capable of tolerating at the reaction temperature. Such a catalyst may includes, for example, triphenylphosphine, tetraphenylphosphonium bromide, tetrabutylphosphonium chloride, triethylsulfonium iodide, triphenylsulfonium bromide, etc. The amount of the catalyst is 0.1–10% by weight, preferably 0.3–5% by weight, based on the halo-phthalic anhydride. Further, the use of an alkali-metal iodide or an alkali-metal fluoride as a co-catalyst allows the reactivity to heighten, and further there is also a merit that the product is little colored. The employable alkali-metal iodide includes LiI, NaI, KI, etc., and the employable alkali-metal fluoride includes LiF, NaF, KF, etc. The amount of the co-catalyst to be employed is 0.05–5% by weight, preferably 0.1–2% by weight, based on the halo-phthalic anhydride.

A solvent is employed in the reaction. The solvent to be employed must have a boiling point near the reaction temperature (170–260° C.) and not participate in the reaction. For example, a polychlorobenzene such as 1,2-dichlorobenzene and 1,2,4-trichlorobenzene, a polychlorotoluene such as 1,2-dichlorotoluene can be employed. A dehydrated aprotic polar solvent, e.g., sulfolane can also be employed. The amount to be employed is 50–600% by weight, preferably 100–200% by weight, based on the halo-phthalic anhydride.

In order to isolate oxy-diphthalic anhydrides, the reaction product is subjected to hot filtering, followed by cooling the resulting filtrate to obtain oxy-diphthalic anhydrides. The filtrate may be concentrated if desired to allow the yield to increase. When sulfolane is employed, after allowing the filtrate to disperse in water, the precipitated oxy-diphthalic acid is subjected to the solid-liquid separation. The resulting oxy-diphthalic acid is ring-closed by heating or employing acetic anhydride to obtain oxy-diphthalic anhydrides.

According to the method of the present invention, since the reaction is carried out in the presence of a solvent, it is hard to produce resin components and to color in comparison with the neat reaction, and therefore the method can save time and labor for decoloration and purification. Accordingly, oxy-diphthalic anhydrides, which are preferable also for the electronic material use where the high purity is required, can be obtained.

EXAMPLES

Example 1

90.8 g (0.4 mol) of 4-bromo-phthalic anhydride and 150 g of 1,2-dichlorotoluene were charged in a reactor to heat at 210° C. Then, 21.2 g (0.20 mol) of granular sodium carbonate having the diameter of 200–500 μm, 4.5 g (0.011 mol) of tetraphenylphosphonium bromide and 2.1 g (0.013 mol) of potassium iodide were charged in the reactor intermittently over 90 minutes, followed by aging for 3 hours after the charge. High performance liquid chromatography test showed 90% of the reaction ratio (yield). The reaction product was cooled to 150° C., followed by hot filtering. After cooling the filtrate, 4-oxy-diphthalic anhydride was isolated (amount: 50.9 g (yield: 82.0%)). Acetic acid is employable to wash if further purification of the product is needed.

Example 2

73.0 g (0.40 mol) of 3-chloro-phthalic anhydride and 200 g of 1,2,4-trichlorobenzene were charged in a reactor to heat at 220° C. Then, 14.8 g (0.20 mol) of granular lithium carbonate having the diameter of 200–500 μm, 3.5 g (0.015 mol) of triethylsulfonium iodide and 1.8 g (0.031 mol) of potassium fluoride were charged intermittently over 90 minutes, followed by aging for 4 hours after the charge. High performance liquid chromatography test showed 88% of the yield. The reaction product was cooled to 150° C., followed by hot filtering. After cooling the filtrate, 3-oxy-diphthalic anhydride was isolated (amount: 49.6 g is (yield: 79.9%)). Acetic acid is employable to wash if further purification of the product is needed.

Example 3

90.8 g (0.40 mol) of 4-bromo-phthalic anhydride and 150 g of dehydrated sulfolane were charged in a reactor to heat at 200° C. Then, 21.2 g (0.20 mol) of granular sodium carbonate having the diameter of 200–500 μm, 4.5 g (0.017 mol) of triphenylphosphine and 2.1 g (0.013 mol) of potassium iodide were charged intermittently over 90 minutes, followed by aging for 4 hours after the charge. High performance liquid chromatography test showed 85% of the yield. The reaction product was cooled to 150° C., followed by hot filtering. The filtrate was subjected to cooling to charge in 500 ml of 5% aqueous acetic acid solution, followed by stirring with heat for 2 hours at 90° C. in order to allow oxy-diphthalic anhydrides to ring-open to obtain a tetracarboxylic acid. After cooling, the product was subjected to the solid-liquid separation, followed by allowing the resulting oxy-diphthalic acid to ring-close by heating in 20 g of 1,2-dichlorobenzene for 3 hours at 220° C. When the ring-closure of the oxy-diphthalic acid has been completed, the state of the system changed from white turbid to the state between transparent and slightly turbid. After hot filtering the product, the filtrate was cooled, followed by isolating 4-oxy-diphthalic anhydride (amount: 49.0 g (yield: 79.0%)). Acetic acid is employable to wash if further purification of the product is needed.

Comparative Example 1

The reaction was carried out under the same conditions as in Example 1, except that the granular potassium carbonate having the diameter of 200–500 μm was employed in place of granular sodium carbonate. The yield of 4-oxy-diphthalic anhydride was 37.1%.

Thus, in comparison with the reaction in which potassium carbonate was employed in the solvent, the method of the present invention provided oxy-diphthalic anhydrides of the product with the higher yield and the simpler reaction.

What is claimed is:

1. A method for preparing oxy-diphthalic anhydrides, which comprises reacting a halo-phthalic anhydride represented by the formula (1):

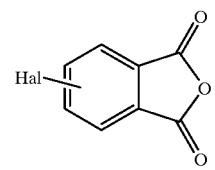

(1)

where Hal represents F, Cl, Br or I, with a carbonate salt selected from the group consisting of lithium carbonate, sodium carbonate, magnesium carbonate and calcium carbonate in a solvent, in the presence of a phosphonium or sulfonium salt which acts as a phase transfer catalyst, and in the presence of an alkali-metal iodide or fluoride which acts as a co-catalyst, to prepare oxy-diphthalic anhydrides represented by the formula (2):

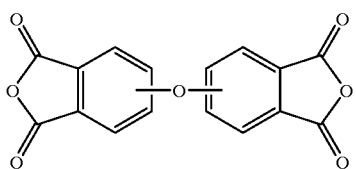

(2)

2. The method according to claim 1, wherein the carbonate salt is magnesium.

3. The method according to claim 1, wherein the carbonate salt is calcium.

4. The method according to claim 1, wherein the carbonate is granular and has a diameter of about 50 to 750 μm.

5. The method according to claim 1, wherein the alkali-metal iodide is at least one selected from the group consisting of lithium iodide, sodium iodide and potassium iodide.

6. The method according to claim 1, wherein the alkali-metal fluoride is selected from the group consisting of lithium fluoride, sodium fluoride and potassium fluoride.

7. The method according to claim 1, wherein said reaction is carried out at the temperature of 170–260° C.

8. The method according to claim 1, wherein the solvent has a boiling point near the reaction temperature, and does not participate in the reaction.

9. The method according to claim 1, wherein the solvent is a dehydrated aprotic polar solvent.

* * * * *